United States Patent [19]

Brossi et al.

[11] 3,946,041

[45] Mar. 23, 1976

[54] 6-(3,4-METHYLENEDIOXY-6-BENZYLALKYLAMINOETHYL-PHENYLACETYL)BENZOIC ACID ALKYL ESTER DERIVATIVES

[75] Inventors: Arnold Brossi, Verona; Wilhelm Kloetzer, East Orange; Sidney Teitel, Clifton, all of N.J.

[73] Assignee: Hoffmann-La Roche Inc., Nutley, N.J.

[22] Filed: Aug. 8, 1973

[21] Appl. No.: 386,668

Related U.S. Application Data

[60] Division of Ser. No. 166,582, July 27, 1971, Pat. No. 3,772,327, which is a continuation-in-part of Ser. No. 141,979, May 10, 1971, abandoned.

[52] U.S. Cl. ............................................. 260/340.5
[51] Int. Cl.² ........................................ C07D 317/68
[58] Field of Search ................................ 260/340.5

[56] References Cited
UNITED STATES PATENTS 2,104,726  1/1938  Addinall et al. ................ 260/340.5
2,189,809  2/1940  Addinall et al. ................ 260/340.5

OTHER PUBLICATIONS

Kelentei et al., Arch. exptl. Pathol. Pharmakol, 233, pp. 550–555 (1958).

Addinall et al., J.A.C.S. 55, pp. 2153–2163, (1933).

Stecher, The Merck Index, 8th Ed., pp. 719–720 (1968).

Morrison et al., Organic Chemistry, 2nd Ed., (1966), pp. 601–603.

Whaley et al., J. Org. Chem. 19, (1954), pp. 666–669.

Primary Examiner—Lorraine A. Weinberger
Assistant Examiner—Michael Shippen
Attorney, Agent, or Firm—Samuel L. Welt; Bernard S. Leon; William G. Isgro

[57] ABSTRACT

The present invention relates to the preparation of novel rheadan-type alkaloids and to novel intermediates useful in the preparation thereof. The process utilizes as starting materials a known class of alkaloids of the narcotine or of the hydrastine type. Certain of the said novel intermediates are also pharmaceutically useful in and of themselves. Additionally, certain of the novel intermediates can be converted into other type alkaloids which are also pharmaceutically useful.

3 Claims, No Drawings

6-(3,4-METHYLENEDIOXY-6-BENZYLALK-YLAMINOETHYLPHENYLACETYL)BENZOIC ACID ALKYL ESTER DERIVATIVES

This is a division, of application Ser. No. 166,582 filed July 27, 1971 now U.S. Pat. No. 3,772,327, issued Nov. 13, 1973, which in turn is a continuation-in-part of application Ser. No. 141,979, filed May 10, 1971, now abandoned.

DETAILED DESCRIPTION OF THE INVENTION

The present invention in more particular detail relates to the preparation of rheadan-type alkaloids of the formula

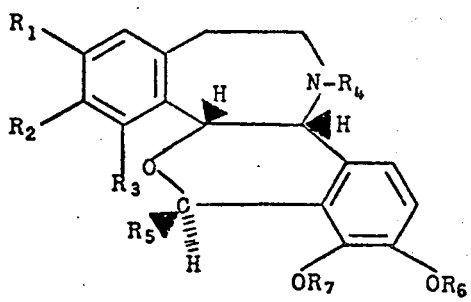

wherein $R_1$ and $R_2$ represent individually lower alkoxy and when taken together lower alkylenedioxy; $R_3$ represents hydrogen and lower alkoxy; $R_4$ represents lower alkyl; $R_5$ represents lower alkoxy and $R_6$ and $R_7$ represent individually lower alkyl and when taken together lower alkylene, certain of which are novel. Specifically compounds of the formula I wherein $R_3$ is lower alkoxy are novel. Also novel are compounds of the formula I in which when $R_3$ is hydrogen either $R_1$ and $R_2$ represent lower alkoxy or $R_6$ and $R_7$ represent lower alkyl.

Such compounds of the formula I lower intraocular pressure and hence are useful in the treatment of glaucoma.

Compounds of the formula I above and III and IV hereinafter form acid addition salts with pharmaceutically acceptable acids such as hydrochloric acid, hydrobromic acid, sulfuric acid, phosphoric acid and the like and organic acids such as chloroethane sulfonic acid. Compounds of the formula I above also form quaternary ammonium salts with conventional quaternizing agents such as lower alkyl and lower alkenyl halides, e.g., mety iodide, allyl bromide, dilower alkyl sulfates, such as dimethylsulfate and the like. Such acid addition salts and quaternary ammonium compounds are included within the purview of the present invention.

As utilized throughout the present invention, the term "lower alkyl" is intended to represent a straight or branched chain saturated hydrocarbon group such as methyl, ethyl, propyl, isopropyl, butyl and the like having 1-4 carbon atoms. Most preferred among the lower alkyl groupings is methyl.

The term "lower alkoxy" as utilized herein comprehends a lower alkyloxy grouping having 1-4 carbon atoms in the chain such as methoxy, ethoxy, propoxy, butoxy and the like. Methoxy is the preferred lower alkoxy group. The expression "lower alkylenedioxy" designates a divalent hydrocarbon chain joined to two oxygen atoms and having 1-4 carbon atoms in the divalent hydrocarbon chain, e.g., methylenedioxy, ethylenedioxy and the like. Methylenedioxy is the most preferred lower alkylenedioxy grouping. Similarly the expression "lower alkylene" represents methylene, ethylene, propylene and the like.

Especially preferred among the compound of the formula I as well as the other formula illustrated hereinafter are those compounds wherein $R_5$ represents methoxy and $R_6$ and $R_7$ each represent methyl. Also preferred are those compounds wherein $R_1$ and $R_2$ represent methoxy or together methylenedioxy and $R_4$ is methyl. Also preferred are compounds wherein $R_3$ is hydrogen and methoxy. Also preferred among the compounds illustrated and described herein are those compounds wherein $R_1$ and $R_2$ when taken together represent methylenedioxy; $R_3$ is selected from the group consisting of hydrogen and methoxy and $R_4$, $R_6$ and $R_7$ is methyl. When the compound includes an $R_5$ grouping, $R_5$ is methoxy preferably. Another preferred group includes $R_6$ and $R_7$ as methylene.

The preparative techniques illustrated above will be more particularly described hereinafter with particular reference to the following diagrammatical flow sheet in which $R_1$, $R_2$, $R_3$, $R_4$, $R_7$ and $R_6$ have the meanings ascribed thereto hereinabove.

FLOW SHEET 1

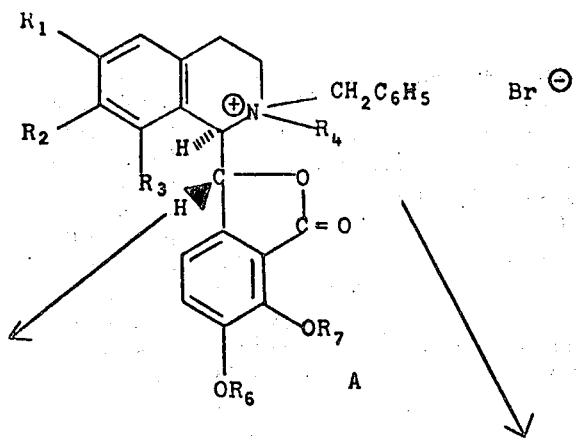

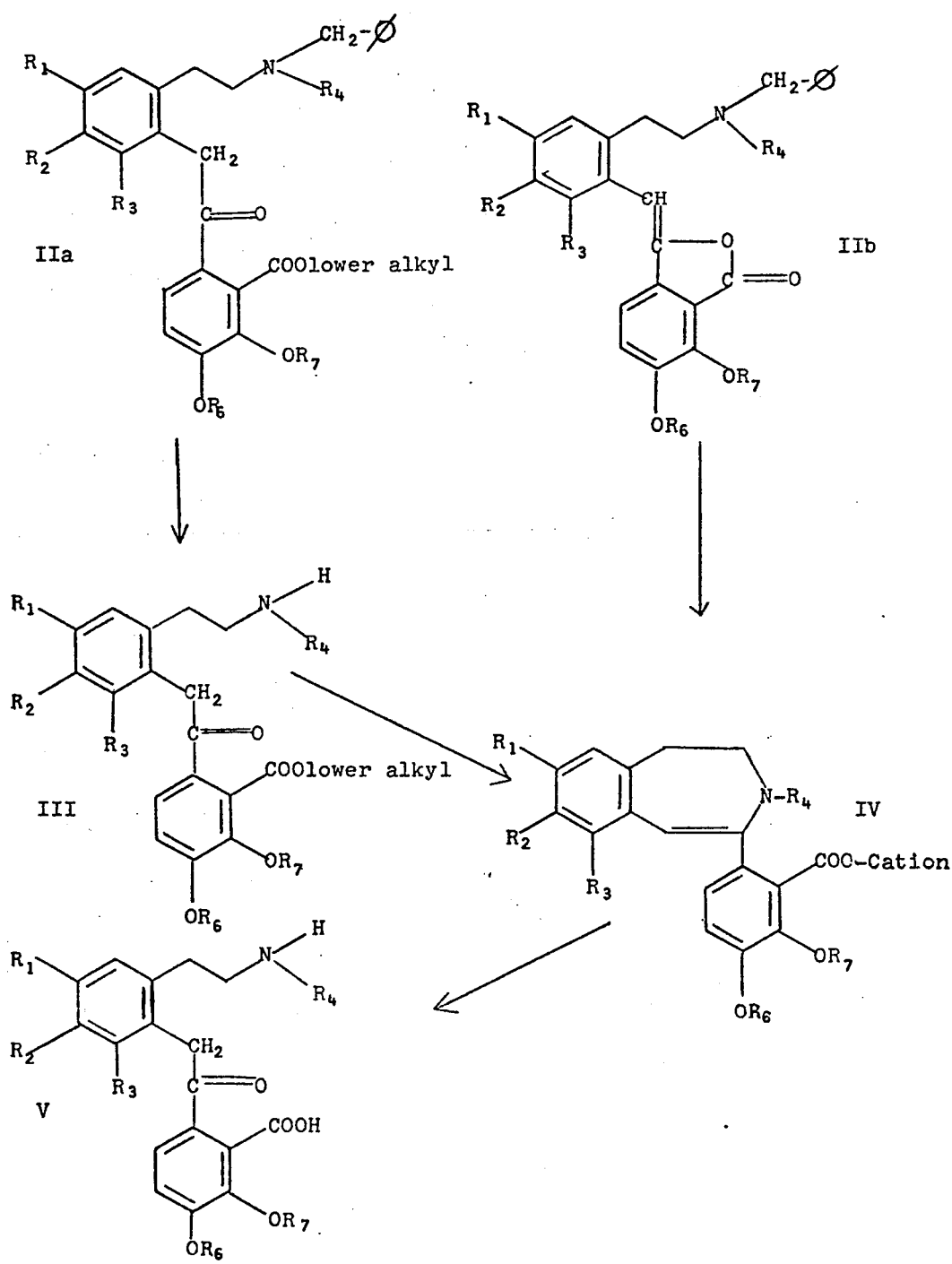

The process illustrated diagrammatically above involves the preparation of key intermediates of the formula IV above. As is indicated in the diagrammatical flow sheet, the compound of the formula IV above may be prepared by varying techniques and converted into alkaloids of varying structures.

For example, in one process route, a quaternary of the narcotine alkaloid type ($R_3$ = alkoxy) or of the hydrastine alkaloid type ($R_3$ = H), Flowsheet I, compound A, is converted into a compound of the formula IIa. In a preferred embodiment, basic solutions are employed in the conversion of the quaternary. Such solutions may be prepared utilizing strong inorganic bases such as alkali metal hydroxides and the like. Basic solutions suitable for the purposes of the present invention may also be provided by organic basic substances, such as ammonia, primary secondary and tertiary amines, e.g., triethylamine, tripropylamine, trimethylamine, ethylamine, methylamine, diethylamine, pyridine, quinoline and the like disposed in aqueous organic solvents, such as aqueous solutions of lower alkanols, e.g., methanol, ethanol, propanol, butanol and the like.

In the most preferred aspect of this process step, the quaternary starting material is treated with a lower alkanolic solution (preferably an ethanolic solution) of a strong organic base such as a tertiaryamine, triethylamine, tripropylamine and the like, most suitably at elevated temperatures, most preferably, at about the reflux temperature of the reaction medium, to effect conversion of the quaternary to the corresponding compound of the formula IIa.

As should be evident from the above diagrammatical flow sheet, the phthalido moiety of the phthalidoisoquinoline nucleus is cleaved under the conditions employed to obtain an N-benzyl narceine-type alkaloid containing an ester grouping (the alkanol providing the lower alkyl portion of the ester moiety). Any conditions capable of effecting this end are suitable for the purposes of the present invention.

The so-obtained compound of the formula IIa is then debenzylated whereby the corresponding compound of the formula III results. This process step is conveniently effected under acidic conditions utilizing any conveniently available hydrogenating agent capable of effecting hydrogenolysis. Suitably the compound of the formula IIa above is employed in salt form. The salt can be formed in a conventional way, for example, utilizing a strong mineral acid such as hydrohalide acid, e.g. hydrochloric acid, sulfuric acid and the like or a strong organic acid, e.g., toluene sulfonic acid and the like. The salt of a compound of the formula IIa above dissolved in an organic solvent such as lower alkanol, e.g., methanol, ethanol, dioxane, THF and the like is then catalytically hydrogenated. Among the suitable catalysts, in the presence of which debenzylation can be effected, there can be included any suitable noble metal catalyst such as palladium, platinum, pd/c and the like.

In a preferred embodiment, the debenzylation is effected under acidic conditions by treatment with hydrogen activated by the presence of a noble metal catalyst such as palladium on carbon. Temperature is not critical to a successful performance of this reaction step but it is preferred to effect the reaction at about room temperature. Further, pressure is not critical but it is preferred to perform the reaction at atmospheric pressure or at moderately elevated pressures, e.g., up to 5 atms. More energetic conditions, e.g., elevated temperatures, should be avoided to lessen the likelihood of the formation of unwanted side products and hence, to obtain the highest yields.

The conversion of a compound of the formula III above to the corresponding compound of the formula IV above is suitably effected by adding a compound of the formula III prepared as described above to a basic solution containing an inorganic strong base such as a metal hydroxide, e.g., alkali metal and alkaline earth metal hydroxides and the like, conveniently contained in an aqueous medium. The so-obtained reaction mixture upon heating results in the preparation of the compound of the formula IV above. The same end can be effected by permitting the reaction medium so prepared to stand at room temperature over a long period of time. Most preferred for this purpose is treating a compound of the formula III with an aqueous solution of a strong alkali metal hydroxide such as aqueous sodium hydroxide, aqueous potassium hydroxide. Also aqueous alkaline earth metal hydroxide can similarly be utilized, e.g., aqueous calcium hydroxide.

As can be seen from the diagrammatical flow sheet, such treatment of the compound of the formula III results in de-esterification of the ester moiety to the corresponding cationic salt and concurrent ring closure to a compound containing a benzazepine nucleus. The cation portion of a compound of the formula IV is illustrated by Na, K, Ca and the like.

In another process aspect, compounds of the formula IV can be prepared from the corresponding compounds of the formula IIb (prepared in an analogous manner to that described in Freund and Lutze, Ber. dltsch. Chem. Ges. 26, 2489) by treating the compounds of the formula IIb with reagents that effect debenzylation and then ring opening of the heterocyclic portion of the phthalido nucleus. Preferably, a debenzylating agent such as phenylchloroformate or cyanogen halide preferably cyanogen bromide may be utilized to effect the debenzylation as illustrated in the diagrammatical flow sheet. Suitably, this reaction is effected in the presence of an inert organic solvent, such as chloroform, methylene chlorine, hydrocarbons, such as benzene, toluene, a chlorinated hydrocarbon ($p$-chlorobenzene) and the like. While temperature and pressure are not critical to a successful performance of this process step, it is preferred to effect the ongoing reaction at temperatures between about 0° and room temperature most preferably, from about 15° to about room temperature. The intermediate so-obtained either with or without isolation from the reaction medium in which it is prepared, can be treated with an aqueous solution of an alkali metal hydroxide such as aqueous sodium hydroxide whereby the corresponding compound of the formula IV above results. The intermediate which contains an acyl moiety on the terminal nitrogen atom and a lactone group is converted by such treatment to the corresponding compound of the formula IV.

Compounds of the formula IV above are key intermediates in the pathway to the corresponding compounds of the formula I above. They also can be converted to other alkaloid-type compounds, some of which are known to be naturally occurring.

In one approach, compounds of the formula IV can be converted into the corresponding compound of the formula V by hydrolysis whereby removal of the alkali metal group illustrated in formula IV is effected and ring opening results. This end can be conveniently effected by hydrolyzing a compound of the formula IV by any conventional technique. For example, a compound of the formula IV can be treated with an aqueous acidic medium such as aqueous hydrohalides, e.g., aqueous hydrochloric acid, aqueous nitric acid, aqueous sulfuric acid and the like. When proceeding accordingly, there results nornarceine type alkaloids ($R_3$ = methoxy) and norhydrastine alkaloids ($R_3$ = H). Norhydrastine type alkaloids are novel and hence constitute a part of the present invention. This reaction is conducted at elevated temperatures, preferably at about 90°C. Also, the aqueous acidic medium should be utilized in excess amounts. , R$_{of\ the\ formula\ V\ are\ useful\ as}$ V are useful as antitussive agents.

The compounds of the formula IV above can be converted to the corresponding compound of the formula I above in the manner illustrated in the following diagrammatical flow sheet. In the flow sheet, $R_1$, $R_2$, $R_3$, $R_4$, $R_5$, $R_6$ and $R_7$ have the meanings ascribed thereto hereinabove.

FLOW SHEET 2
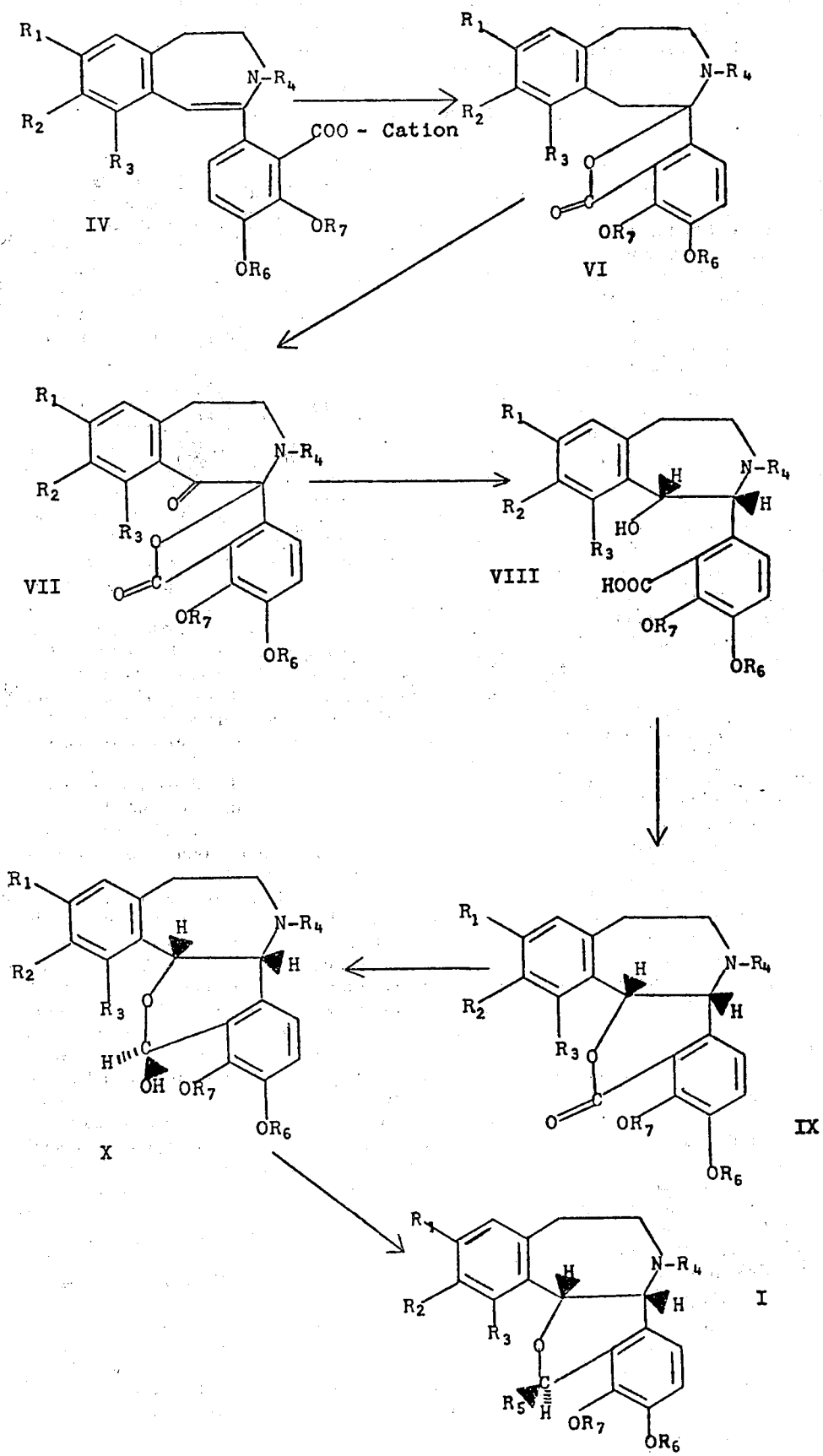

As illustrated in Flow Sheet 2, the compound of the formula IV, as prepared above, is treated with a suitable reagent capable of effecting ring closure to the corresponding compound of the formula VI above. Suitably, the ring closure is effected by the treatment of a compound of the formula IV with an excess of a weak acid, such as a lower alkanoic acid, acetic acid, propionic acid, butyric acid and the like or equivalent molar amounts of a strong mineral acid, e.g., hydrohalic acid, e.g., hydrochloric acid, sulfuric acid and the like. Efficaciously the reaction is effected in the presence of a solvent medium, such as an aqueous medium, e.g., water per se or an aqueous alkanol such as aqueous methanol, aqueous ethanol or any suitable water miscible solvent. Suitably, the reaction is permitted to proceed by permitting it to stand at room temperature for a short period of time.

In the next step, the so-obtained compound of the formula VI is oxidized to the corresponding compound of the formula VII.

The ease in which this oxidation is effected is indeed surprising. Thus, by adding the compound of the formula VI to an inert organic solvent such as methanol, e.g., ethanol, preferably, heated, e.g., hot ethanol and then by permitting the so-obtained reaction medium to stand a compound of the formula VII results. Preferably, to increase the yield, the medium is permitted to stand for two days or longer whereby oxidation of the compound of the formula VI results to the corresponding compound of the formula VII. The oxidation can be accelerated by the use of more energetic oxidizing conditions. For example, by the simple expedient of bubbling air through the reaction medium containing the compound of the formula VI, oxidation can be accelerated. Similarly, the reaction can be also effected in short periods of time by adding to the solution of a compound of the formula VI, a mild oxidizing agent such as hydrogen peroxide or similar type peroxide or selenium dioxide and the like.

In the next process step, a compound of the formula VII is converted into the corresponding compound of the formula VIII by the treatment with a mild reducing agent. Suitably, the reduction is effected by adding a compound of the formula VII to an inert organic solvent such as anhydrous tetrahydrofuran, dimethylformamide, ether, such as diethylether, benzene, toluene, dimethylsulfoxide and the like and adding to the resultant solution a metal borohydride or a metal aluminum hydride. Among the many metal borohydrides suitable for the purposes of the invention, there are preferably utilized alkali metal borohydrides such as sodium borohydride and lithium borohydride or an alkaline earth metal borohydride such as magnesium borohydride, calcium borohydride and the like. Alkali metal aluminum hydride, such as lithium aluminum hydride can also be utilized. Preferred is $LiBH_4$. Temperature and pressure are not critical to a successful performance of this process step. However, in a preferred embodiment, the reaction is effected at room temperature or when alkali metal aluminum hydride is utilized, lower temperatures are preferred, e.g., about 0°.

The so-obtained compound of the formula VIII is then treated with any conveniently available dehydrating agent, preferably, an acidic dehydrating agent which will effect removal of water and concurrent cyclization to a compound of the formula IX above. Preferably, the acidic dehydrating agent utilized is acetic anhydride. However, other suitable dehydrating agents can include phthalic anhydride, chloroacetic acid, malonic anhydride, $N_1N_1$-disubstituted carbodiimide and the like. The compound of the formula IX above can be converted into the corresponding compound of the formula X above by reduction with a suitable mild reducing agent. For this purpose there can be utilized alkali metal alkoxy-aluminum hydrides. such as sodium-bis-methoxy ethoxy aluminum hydride, sodium bisisopropyl aluminum hydride and the like. Preferably, sodium-bis-methoxy ethoxy aluminum hydride is preferred. Suitably, the reduction is effected below room temperature in the presence of an inert organic solvent such as pyridine, tetrahydrofuran and the like.

The so-obtained compound of the formula X upon treatment with an alkylating system which includes tri-lower alkyl orthoformate, e.g., trimethylorthoformate or a system consisting of absolute lower alkanol and a catalytic amount of acid or mixtures of the two systems is then converted into the corresponding compound of the formula I. This reaction is suitably effected in the presence of methanol and in the presence of acid catalyst such as catalytic amounts of concentrated mineral acids, e.g., concentrated sulfuric acid or an aprotic Lewis acid such as boron trifluoride, aluminum trichloride and the like. By proceeding accordingly, there is obtained the corresponding compound of the formula I. The appropriate alkanol utilized will determine the nature of the alkoxy group at $R_5$. Thus, if methanol is utilized, $R_5$ will be methoxy and if ethanol is utilized $R_5$ will be ethoxy, etc.

When proceeding from the compound of the formula VII to the corresponding compound of the formula VIII, it has been observed that an isomer comprising the cis and trans form of a compound of the formula VIII can be obtained. It has been further observed that by varying the reaction conditions, the proportionate amounts of cis and trans isomers formed can be varied.

For example, as described above, when an alkali-metal borohydride is utilized as part of the reducing system, the cis compound is obtained as the predominant product and minor amounts of the corresponding trans compound of the formula

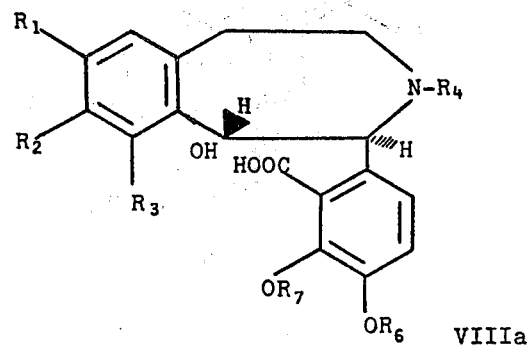

VIIIa wherein $R_1$, $R_2$, $R_3$, $R_4$, $R_6$ and $R_7$ are as above result. The two forms can be separated from the reaction medium in which they are prepared by conventional procedures.

Upon treatment of a compound of the formula VII above under more energetic conditions as described above, the proportionate amount of the trans isomer obtained during the ensuing reaction can be increased.

For example, if a compound of the formula VII above is treated as described above under more severe reducing conditions, e.g., hydrogenation under high pressure in the presence of a catalyst such as a noble metal catalyst, e.g., platinum oxide, palladium on carbon and the like, the yield of the corresponding trans isomer of the formula VIIIa above can be increased. Suitably, the reaction is effected at a pressure of 50–150 atms, most preferably, at about 100 atms and in the presence of a solvent which functions to activate the catalyst in such a way that the reaction is promoted. Preferably, acetic acid is utilized as the solvent medium.

The resultant compound of the above formula VIIIa can be readily converted into the corresponding compound of the formula IX above by treating the same with a strong mineral acid such as hydrochloric acid, preferably disposed in an aqueous medium for a period of several hours. Preferably, 1N-Hydrohalic acid, (1N-Hydrochloric acid) is utilized. Conveniently, the conversion can be effected by adding a compound of the formula VIIIa above to an aqueous solution of a mineral acid such as aqueous hydrochloric acid, aqueous hydrobromic acid and the like and then permitting the reaction medium to stand at room temperature. While performing the transformation of a compound of the formula VIIIa to the corresponding compound of the formula IX above is preferably effected at room temperature, the reaction in a broader aspect can be effected at a temperature from about 0° to about 40°, most preferably from about 20° to about 30°C.

Another preparative approach to the compound of the formula IV above involves in a first stage the treatment of a compound of the formula

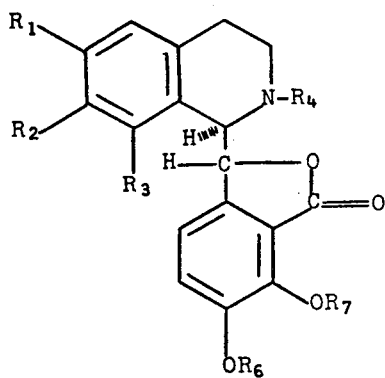

wherein $R_1$, $R_2$, $R_3$, $R_4$, $R_6$ and $R_7$ are as above with a reagent that effects ring opening of the heterocyclic portion of the isoquinoline nucleus and subsequent dehydrohalogenation. When proceeding accordingly, there is obtained an intermediate which contains an acyl moiety on the terminal nitrogen group in addition to a lactone group such as is obtained when a compound of the formula IIb is converted into the corresponding compound of the formula IV. Such compound has the formula

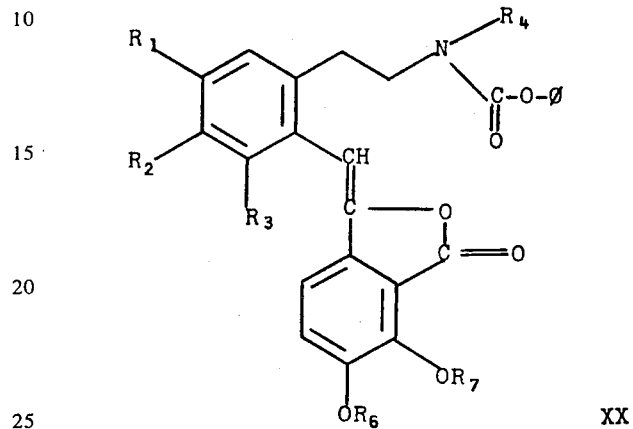

XX wherein $R_1$, $R_2$, $R_3$, $R_4$, $R_6$ and $R_7$ are as above. Preferably, a reagent system comprising phenyl chloroformate in conjunction with a (ditertiary-lower alkyl)-lower alkyl amine, e.g., diisopropylethylamine, in a first step, effects ring opeing and a subsequent reagent system in a second step completes dehydrohalogenation whereby the compound of the formula XX results. In the second step, a ditertiary-lower alkyl-lower alkyl amine and dimethylsulfoxide comprise the reagent system. Suitably, said first step is effected in the presence of an inert organic solvent such as chloroform, methylene chloride, hydrocarbons, such as, benzene, toluene; chlorinated hydrocarbons (p-chlorobenzene) and the like. In the second step, dimethylsulfoxide is utilized as the solvent medium. While temperature and pressure are not critical to a successful performance of this process step, it is preferred to effect the ongoing reaction from about 5° to about room temperature, most preferably from about 15° to about room temperature.

The so-obtained compound of the formula XX above can be treated with an aqueous solution of alkali metal hydroxide such as aqueous sodium hydroxide whereby the corresponding compound of the formula IV above results.

The compounds of the formula I, III and V and their acid addition salts with pharmaceutically acceptable acids and their quaternary of salts with conventional non-toxic quaternizing salt forming agents have valuable therapeutic properties. Compounds of the formula I are useful in the treatment of glaucoma. Compounds of the formula V are useful as antitussive agents. Compounds of the formula III are useful as sedative agents.

Compounds of the formula I, III and V above can be administered parenterally with dosage adjusted to individual requirements, for example, in the form of pharmaceutical preparations which contain the base or their pharmaceutically acceptable addition salts in admixture with pharmaceutical organic or inorganic inert carrier material, for example, water, gelatin, lactose, starch, magnesium stearate, talc, vegetable oils, gums, polyalkylene glycols and the like. The pharmaceutical preparations can be present in solid forms (for example, as tablets, dragees, suppositories, capsules) or if desired, in liquid form, for example, a solution or suspension. The pharmaceutical dosage forms can be sterilized and/or contain additive materials, such as preservatives, stabilization, wetting agents or emulsifying agents, salts for varying the osmotic pressure or buffers. They may also contain other therapeutically valuable material. They can be administered with dosages adjusted to fit the exergencies of a therapeutic situation.

The following examples are illustrative but not limitative of the invention. Various modifications thereof would be apparent to those skilled in the art and are included within the purview of the present invention. All temperatures are stated in degrees centigrade.

EXAMPLE 1

140 g of N-benzyl-1-α-narcotiniumbromide was refluxed with a mixture of 800 ml alcohol and 77 ml triethylamine for 6 hr. After evaporation of ca. 20% of the solvent and cooling, 2,3-dimethoxy-6-(2-methoxy-3,4-methylenedioxy-6-benzylmethylaminoethyl-phenylacetyl)benzoic acid ethyl ester of mp 102°–104° was isolated. A further crop, of the same compound was isolated after evaporation of the other liquor to dryness, dissolving the residue in chloroform, shaking with excess 1NNaOH, evaporation of the chloroform solution and crystallizing the residue from ethanol.

In a similar manner, 2,3-dimethoxy-6-(3,4-methylenedioxy-6-benzylmethylaminoethylphenylacetyl)-benzoic acid ethyl ester was prepared.

EXAMPLE 2

73.7 g of 2,3-dimethoxy-6-(2-methoxy-3,4-methylenedioxy-6-benzylmethylaminoethylphenylacetyl)-benzoic acid ethyl ester as the HCl salt (mp 160°–161°C) was dissolved in 1.8 l. of ethanol. The resulting mixture was hydrogenated in the presence of 11.5 g of 10% Pd/C at 3 atm for 20 hr. After removal of the catalyst, the solution was concentrated to a small volume. After cooling, 2,3-dimethoxy-6-(2-methoxy-3,4-methylenedioxy-6-methylaminoethyl-phenylacetyl)benzoic acid ethyl ester hydrochloride of mp 199°–200° was isolated.

In a similar manner, 2,3-dimethoxy-6-(3,4-methylenedioxy-6-methylaminoethylphenylacetyl)benzoic acid ethyl ester hydrochloride was prepared.

EXAMPLE 3

63 g of 2,3-dimethoxy-6-(2-methoxy-3,4-methylenedioxy-6-methylaminoethylphenylacetyl)benzoic acid ethyl ester hydrochloride and 630 ml of 2N-NaOH was heated on a steambath with stirring for 3 hours. After cooling the solution overnight, 6-(8,9-dihydro-4-methoxy-7-methyl-7H-1,3-dioxolo[4,5-h][3]benzazepin-6-yl)-2,3-dimethoxy benzoic acid sodium salt, m.p. 190°–195° was isolated.

In a similar manner there was prepared 6-(8,9-dihydro-7-methyl-7H-1,3-dioxolo[4,5-h][3]benzazepin-6-yl)-2,3-dimethoxy benzoic acid sodium salt.

EXAMPLE 4

A solution of 0.946 g. of 6,7-dimethoxy-3-[3,4-methylenedioxy-6-(2-benzylmethylaminoethyl)ben- zylidene]phthalide (mp 135°, prepared according to M. and F. Lutze, Ber. dltsch. chem. ces. 26, 2489) in 20 ml. of chloroform was treated with 0.4 g. of phenyl chloroformate at 20° overnight. After evaporated of the solvent, the residue was washed with 10 ml. of ether. The solid residue was heated with 10 ml. of 2N-NaOH for 2 hours on a steam bath. On cooling, 6-[8,9-dihydro-7-methyl-7[H]-1,3-dioxolo-[4,5-h][3]-benzazepin-azepin-6-yl]-2,3-dimethoxy benzoic acid sodium salt, mp 230° dec. was isolated.

In a similar manner 6-[8,9-dihydro-7-methyl-4-methoxy-7H-1,3-dioxolo[4,5-h][3]-benzazepin-6-yl]-2,3-dimethoxy benzoic acid sodium salt.

EXAMPLE 5

A solution of 1.1 g. of 6-[8,9-dihydro-4-methoxy-7-methyl-7H-1,3-dioxolo[4,5-h][3]-benzazepin-6-yl]-2,3-dimethoxy benzoic acid sodium salt in 15 ml. of $H_2O$ was acidified with 20% of HCl to pH 1 and heated 30 minutes on a steam bath. The solution was then adjusted to pH 7-8 with $NaHCO_3$ to precipitate 2,3-dimethoxy-6-(2-methoxy-3,4-methylenedioxy-6-methylamino ethylphenylacetyl)benzoic acid, mp 225°–229°.

EXAMPLE 6

A solution of 0.3 g. of 6-[8,9-dihydro-7-methyl-7H-1,3-dioxolo-[4,5-h][3]-benzazepin-6-yl]-2,3-dimethoxy benzoic acid sodium salt in 4 ml. of 2N HCl was heated for 30 minutes on a steam bath. Neutralization of the solution to pH 7-8 gave 2,3-dimethoxy-6-(3,4-methylenedioxy-6-methylaminoethylphenylacetyl) benzoic acid, mp 176°–179°.

EXAMPLE 7

To a solution of 55 g. of 6-[8,9-dihydro-4-methoxy-7-methyl-7H-1,3-dioxolo[4,5-H][3]benzazepin-6-yl]-2,3-dimethoxybenzoic acid sodium salt in 300 ml. of $H_2O$ was added 15 ml. of glacial acetic acid. After 10 minutes the precipitated 4,4',5trimethoxy-7'-methyl-5', 7', 8', 9'-tetrahydrospiro[phthalan-1,6'1,3-dioxolo[4,5-h][3]-benzazepine]-3-one was isolated, mp 169°–171°.

EXAMPLE 8

A solution of 0.5 g. of 6-[8,9-dihydro-7-methyl-7H-1,3-dioxolo-[4,5-h][3]-benzazepin-6-yl]-2,3-dimethoxy benzoic acid sodium salt in 5 ml. of water was acidified with 10% acetic acid and the precipitate extracted with methylene chloride and the extract evaporated. The residue was recrystallized from ether to afford 4,5-dimethoxy-7'-methyl-5', 7', 8', 9'-tetrahydrospiro[phthalan-1,6'-1,3-dioxolo[4,5-h][3]-benzazepine]-3-one, mp. 130°–132°.

EXAMPLE 9

A solution of 43.5 g. of 4,4',5-trimethoxy-7'-methyl-5', 7', 8', 9'-tetrahydrospiro[phthalan-1,6'-1,3-dioxolo[4,5-h][3]-benzazepine]-3-one dissolved in 2.8 l. of hot ethanol was stored at 25° in open flasks for 10 days. The crystals that formed were collected, washed with ethanol and dried to give 4,4′,5-trimethoxy-7′-methyl-8′, 9′-dihydrospiro[phthalan-1,6′-1,3-dioxolo]4,5-h][3]benzazepine]-3,5′(7′H)-dione of mp 186°–190°.

EXAMPLE 10

A solution of 700 mg. of 4,5-dimethoxy-7′-methyl-5′, 7′, 8′, 9′-tetrahydrospiro[phthalan-1,6′-1,3-dioxolo[4,5-h][3]-benzazepine]-3-one, in 35 ml. of ethanol was kept in an open flask for 2 days at 25°. Filtration supplied 4,5-dimethoxy-7′-methyl-8′, 9′-dihydrospiro[phthalan-1,6′-1,3-dioxolo[4,5-h][3]-benzazepine]-3,5′(7′H)-dione, mp 123°–126° (from ether).

EXAMPLE 11

To a solution of 20 g. of 4,4′,5′-trimethoxy-7′-methyl-8′, 9′-dihydrospiro[phthalan-1,6′-1,3-dioxolo[4,5-h][3]benzazepine]-3,5′(7′H)-dione in 600 ml. of dry THF a solution of 3.6 g. of LiBH$_4$ in 250 ml. of THF was added dropwise with stirring and cooling (ice bath). After standing overnight at 25°, the solvent was evaporated under reduced pressure, and the residue heated with 150 ml. of H$_2$O for 10 minutes on a steam bath. After standing at room temperature for 2 hours, the solution was filtered and after addition of 20 ml. of acetic acid (glacial) the solution was heated for 20 minutes on a steam bath. The precipitated, 5,6-cis-6-[5-hydroxy-6,7,8,9-tetrahydro-4-methoxy-7-methyl-5H-1,3-dioxolo[4,5-h][3]benzazepin-6-yl]-2,3-dimethoxy benzoic acid was isolated after cooling to room temperature, mp 258°–260° dec. The filtrate on standing at room temperature for 6 hours separated 2 g of 5,6-trans-6-(5-hydroxy-6,7,8,9-tetrahydro-4-methoxy-7-methyl-5H-1,3-dioxolo[4,5][3]benzazepin-6-yl)-2,3-dimethoxy benzoic acid mp 225° dec. (from ethanol).

EXAMPLE 12

A mixture of 1.6 g. of 5,6-cis-6-[5-hydroxy-6,7,8,9-tetrahydro-4-methoxy-7-methyl-5H-1,3-dioxolo[4,5-h][3]benzazepin-6-yl]-2,3-dimethoxy benzoic acid and 30 ml. of acetic anhydride was heated for 2 hours on a steam bath and evaporated to dryness under reduced pressure. The residue was dissolved in CH$_2$Cl$_2$ extracted with cold 1N-NaOH and the organic layer evaporated to afford cis-4b,10b-2,3-methylenedioxy-4,7,8-trimethoxy-6-oxo-11-methylrheadan, mp 218°–220° (from EtOH).

EXAMPLE 13

A solution of 8 g. of cis-4b,10b-2,3-methylenedioxy-4,7,8-trimethoxy-6-oxo-11-methylrheadan in 250 ml. of dry pyridine was reduced at 4° by the addition of 6.52 ml. of a 70% solution of sodium bis-(2-methoxyethoxy)aluminum hydride in benzene diluted with 55 ml. of dry THF over 3 hours. After addition of 15 ml. of methanol, the solvent was removed under reduced pressure at 50°. The residue was treated with a mixture of 25 ml. of methanol and 10 ml. of 1N-NaOH on a steam bath for 10 minutes. After evaporation of the solvent, the residue was dissolved in CH$_2$Cl$_2$ and washed with water. The residue of the organic layer crystallized on addition of ether to give cis-4b,10b-2,3-methylenedioxy-4,7,8-trimethoxy-6-hydroxy-11-methylrheadan, mp 224°–226° (from methanol).

EXAMPLE 14

To a suspension of 1 g of cis-4b,10b-2,3-methylenedioxy-4,7,8-trimethoxy-6-hydroxy-11-methylrheadan in 50 ml of absolute methanol was added 3 ml of trimethylorthoformate and 0.23 g of conc. H$_2$SO$_4$. The solution was stirred under N$_2$ for 14 hr. After removal of the solvent at 40°, the residue was treated with aqueous K$_2$CO$_3$ solution and extracted with ethyl acetate. The residue of the organic layer was crystallized from ether to give cis-4b,10b-2,3-methylenedioxy-4,6,7,8-tetramethoxy-11-methylrheadan, mp 137°–138°.

In a similar manner to that described in this and the preceding Examples, starting with the compound prepared as described in Example 10, there could be prepared cis-4b,10b-2,3-methylenedioxy-6,7,8-trimethoxy-11-methylrheadan. When proceeding accordingly, there can be prepared as intermediates:

5,6-cis-6-[5-hydroxy-6,7,8,9-tetrahydro-7-methyl-5H-1,3-dioxolo[4,5-h][3]benzazepin-6-yl]-2,3-dimethoxy benzoic acid which can be converted into cis-4b,10b-2,3-methylenedioxy-7,8-dimethoxy-6-oxo-11-methylrheadan which can be converted into cis-4b,10b-2,3-methylenedioxy-7,8-dimethoxy-6-hydroxy-11-methylrheadan.

EXAMPLE 15

Parenteral Formulation

|  | Per cc: |
|---|---|
| 2,3-Dimethoxy-6-(3,4-methylenedioxy-6-methyl-aminoethylphenyl-acetyl)benzoic acid | 5.0 mg. |
| Propylene Glycol | 0.4 cc. |
| Benzyl Alcohol (Benzaldehyde free) | 0.15 cc. |
| Ethanol 95% U.S.P. | 0.1 cc. |
| Water for Injection q.s. | 1.0 cc. |

Procedure (For 10,000 cc):

1. The 50 grams of 2,3-dimethoxy-6-(3,4-methylenedioxy-6-methylaminoethylphenyl-acetyl)benzoic acid were dissolved in the benzyl alcohol; 4,000 cc. of propylene glycol and 1,000 cc. of ethanol were added.

2. The solution was brought up to final volume of 10,000 cc. with Water for Injection.

3. The solution was filtered through an 0.2 Selas candle, filled into suitable size ampuls, gassed with nitrogen and sealed.

EXAMPLE 16

Tablet Formulation

|  | Per Tablet |
|---|---|
| 2,3-Dimethoxy-6-(3,4-methylenedioxy-6-methyl-aminoethylphenyl-acetyl)benzoic acid | 10.0 mg. |
| Lactose | 113.5 mg. |
| Corn Starch | 70.5 mg. |
| Pregelatinized Corn Starch | 8.0 mg. |
| Calcium Stearate | 3.0 mg. |
| Total Weight | 205.0 mg. |

Procedure:

1. 2,3-Dimethoxy-6-(3,4-methylenedioxy-6-methylaminoethylphenylacetyl)benzoic acid was mixed with the lactose, corn starch and pregelatinized corn starch in a suitable size mixer.

2. The mix was passed through a Fitzpatrick Comminuting Machine fitted with No. 1A screen and with knives forward.

3. The mix was returned to the mixer and moistened with water to a thick paste. The moist mass was passed through a No. 12 screen and the moist granules were dried on paper lined trays at 110° F.

4. The dried granules were returned to the mixer, the calcium stearate was added and mixed well.

5. The granules were compressed at a tablet weight of 200 mg. using standard concave punches having a diameter of 5/16 inch.

EXAMPLE 17

Tablet Formulation

|  | Per Tablet |
|---|---|
| 2,3-Dimethoxy-6-(3,4-methylenedioxy-6-methyl-aminoethylphenyl-acetyl) benzoic acid | 25.00 mg. |
| Lactose, U.S.P. | 64.50 mg. |
| Corn Starch | 10.00 mg. |
| Magnesium Stearate | 0.50 mg. |

Procedure:

1. 2,3-Dimethoxy-6-(3,4-methylenedioxy-6-methylaminoethylphenylacetyl)benzoic acid was mixed with the lactose, corn starch and magnesium stearate in a suitable mixer.

2. The mixture was further blended by passing through a Fitzpatrick Comminuting Machine fitted with a No. 1A screen with knives forward.

3. The mixed powders were slugged on a tablet compressing machine.

4. The slugs were comminuted to a suitable mesh size (No. 16 screen) and mixed well.

5. The tablets were compressed at a tablet weight of 100 mg. using tablet punches having a diameter of approximately ¼ inch. (Tablets may be either flat or biconvex and may be scored if desired.)

EXAMPLE 18

Capsule Formulation

|  | Per Capsule |
|---|---|
| 2,3-Dimethoxy-6-(3,4-methylenedioxy-6-methyl-aminoethylphenyl-acetyl)benzoic acid | 25 mg. |
| Lactose | 158 mg. |
| Corn Starch | 37 mg. |
| Talc | 5 mg. |
| Total Weight | 255 mg. |

Procedure:

1. 2,3-dimethoxy-6-(3,4-methylenedioxy-6-methylaminoethylphenylacetyl)benzoic acid was mixed with the lactose and corn starch in a suitable mixer.

2. The mixture was further blended by passing through a Fitzpatrick Comminuting Machine with a No. 1A screen with knives forward.

3. The blended powder was returned to the mixer, the talc added and blended thoroughly. The mixture was then filled into No. 4 hard shell gelatin capsules on a Parke Davis capsulating machine. (Any similar type machine may be used.)

EXAMPLE 19

Capsule Formulation

|  | Per Capsule |
|---|---|
| 2,3-Dimethoxy-6-(3,4-methylenedioxy-6-methyl-aminoethylphenyl-acetyl)benzoic acid | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:

1. 2,3-Dimethoxy-6-(3,4-methylenedioxy-6-methylaminoethylphenylacetyl)benzoic acid was mixed with the lactose and corn starch in a suitable mixer.

2. The mixture was further blended by passing through a Fitzpatrick Comminuting Machine with a No. 1A screen with knives forward.

3. The blended powder was returned to the mixer, the talc added and blended thoroughly. The mixture was then filled into No. 4 hard shell gelatin capsules on a Parke Davis Capsulating Machine. (Any similar type machine may be used.)

EXAMPLE 20

Parenteral Formulation

|  | Per cc: |
|---|---|
| Cis-4b,10b-2,3-methylenedioxy-4,6,7,8-tetramethoxy-11-methylrheadan | 5.0 mg. |
| Propylene Glycol | 0.4 cc. |
| Benzyl Alcohol (Benzaldehyde free) | 0.15 cc. |
| Ethanol 95% U.S.P. | 0.1 cc. |
| Water for Injection q.s. | 1.0 cc. |

Procedure (For 10,000 cc):

1. The 50 grams of Cis-4$b$,10$b$-2,3-methylenedioxy-4,6,7,8-tetramethoxy-11-methylrheadan were dissolved in the benzyl alcohol; 4,000 cc. of propylene glycol and 1,000 cc. of ethanol were added.

1. The solution was brought up to final volume of 10,000 cc. with Water for Injection.

3. The solution was filtered through an 0.2 Selas candle, filled into suitable size ampuls, gassed with nitrogen and sealed.

EXAMPLE 21

Tablet Formulation

|  | Per Tablet |
|---|---|
| Cis-4b,10b-2,3-methylenedioxy-4,6,7,8-tetramethoxy-11-methylrheadan | 10.0 mg. |
| Lactose | 113.5 mg. |
| Corn Starch | 70.5 mg. |
| Pregelatinized Corn Starch | 8.0 mg. |
| Calcium Stearate | 3.0 mg. |
| Total Weight | 205.0 mg. |

Procedure:

1. Cis-4$b$,10$b$-2,3-methylenedioxy-4,6,7,8-tetramethoxy-11-methylrheadan was mixed with the lactose, corn starch and pregelatinized corn starch in a suitable size mixer.

2. The mix was passed through a Fitzpatrick Comminuting Machine fitted with No. 1A screen and with knives forward.

3. The mix was returned to the mixer and moistened with water to a thick paste. The moist mass was passed through a No. 12 screen and the moist granules were dried on paper lined trays at 110° F.

4. The dried granules were returned to the mixer, the calcium stearate was added and mixed well.

5. The granules were compressed at a tablet weight of 200 mg. using standard concave punches having a diameter of 5/16 inch.

EXAMPLE 22

Tablet Formulation

| | Per Tablet |
|---|---|
| Cis-4b,10b-2,3-methylenedioxy-4,6,7,8-tetramethoxy-11-methylrheadan | 25.00 mg. |
| Lactose, U.S.P. | 64.50 mg. |
| Corn Starch | 10.00 mg. |
| Magnesium Stearate | 0.50 mg. |

Procedure:
1. Cis-4b,10b-2,3-methylenedioxy-4,6,7,8-tetramethoxy-11-methylrheadan was mixed with the lactose, corn starch and magnesium stearate in a suitable mixer.
2. The mixture was further blended by passing through a Fitzpatrick Comminuting Machine fitted with a No. 1A screen with knives forward.
3. The mixed powders were slugged on a tablet compressing machine.
4. The slugs were comminuted to a suitable mesh size (No. 16 screen) and mixed well.
5. The tablets were compressed at a tablet weight of 100 mg. using tablet punches having a diameter of approximately ¼ inch. (Tablets may be either flat or biconvex and may be scored if desired.)

EXAMPLE 23

Capsule Formulation

| | Per Capsule |
|---|---|
| Cis-4b,10b-2,3-methylenedioxy-4,6,7,8-tetramethoxy-11-methylrheadan | 25 mg. |
| Lactose | 158 mg. |
| Corn Starch | 37 mg. |
| Talc | 5 mg. |
| Total Weight | 255 mg. |

Procedure:
1. Cis-4b,10b-2,3-methylenedioxy-4,6,7,8-tetramethoxy-11-methylrheadan was mixed with the lactose and corn starch in a suitable mixer.
2. The mixture was further blended by passing through a Fitzpatrick Comminuting Machine with a No. 1A screen with knives forward.
3. The blended powder was returned to the mixer, the talc added and blended thoroughly. The mixture was then filled into No. 4 hard shell gelatin capsules on a Parke Davis capsulating machine. (Any similar type machine may be used.)

EXAMPLE 24

Capsule Formulation

| | Per Capsule |
|---|---|
| Cis-4b,10b-2,3-methylenedioxy-4,6,7,8-tetramethoxy-11-methylrheadan | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:
1. Cis-4b,10b-2,3-methylenedioxy-4,6,7,8-tetramethoxy-11-methylrheadan was mixed with the lactose and corn starch in a suitable mixer.
2. The mixture was further blended by passing through a Fitzpatrick Comminuting Machine with a No. 1A screen with knives forward.
3. The blended powder was returned to the mixer, the talc added and blended thoroughly. The mixture was then filled into No. 4 hard shell gelatin capsules on a Parke Davis Capsulating Machine. (Any similar type machine may be used.)

EXAMPLE 25

To a stirred suspension of 32.8 g of 1-hydrastine in 400 ml of benzene was added 16.4 g of diisopropylethylamine followed by 23.8 g of phenylchloroformate and stored for 16 hours. The resulting solution was evaporated under reduced pressure. To the residue was added 100 ml of dimethylsulfoxide and 16.4 g of diisopropylethylamine and the solution was heated on a steam bath for 4 hours. The cooled solution was diluted with 150 ml water and the mixture distributed in a mixture of 100 ml of ether and 40 ml of ethyl acetate. After separation of the clear aqueous layer, the solids in the organic layer was filtered to afford 6,7-dimethoxy-3[3,4-methylenedioxy-6-(2-phenoxycarbonyl-2-methylaminoethyl)]benzylidene phthalide, m.p. 163°–164° (from EtOH).

EXAMPLE 26

A mixture of 7.7 g of (1)-bicuculline, 2.71 g of diisopropylethylamine and 6.7 g phenylchloroformate in 125 ml of benzene was treated in the same manner as described in Example 25. After evaporation of the solvent, 30 ml of dimethylsulfoxide and 2.71 ml of diisopropylethylamine were added and treated as described in Example 25 to give 6,7-methylenedioxy-3[3,4-methylenedioxy-6-(2-phenoxycarbonyl-2-methylaminoethyl)]benzylidene phthalide, m.p. 204°–206° (from EtOH).

EXAMPLE 27

A mixture of 42 g of 6,7-dimethoxy-3[3,4-methylenedioxy-6-(2-phenoxycarbonyl-2-methylaminoethyl)]benzylidene phthalide, 420 ml of 2N-sodium hydroxide, and 100 ml of tetrahydrofuran was stirred on a steam bath under nitrogen for 4 hours and then the tetrahydrofuran evaporated in a stream of nitrogen. The aqueous solution was stored overnight at 4° and the resulting crystals filtered to give 6(8,9-dihydro-7-methyl-7H-1,3-dioxolo-[4,5-$h$][3]-benzazepin-6-yl]-2,3-dimethoxy benzoic acid sodium salt.

EXAMPLE 28

In an analogous manner as that described in Example 27, 8.45 g of 6,7-methylenedioxy-3[3,4-methylenedioxy-6-(2-phenoxycarbonyl-2-methylaminoethyl)benzylidene phthalide, 20 ml tetrahydrofuran and 84 ml 2N-NaOH afforded 6(8,9-dihydro-7-methyl-7H-1,3-dioxolo[4,5$h$][3]benzazepin-6-yl]2,3-methylenedioxy benzoic acid sodium salt, dec. >250°.

EXAMPLE 29

To a solution of 2.8 g of 6(8,9-dihydro-7-methyl-7H-1,3-dioxolo[4,5-$h$][3]benzazepin-6yl)2,3-methylenedioxy benzoic acid sodium salt in 70 ml of warm water was added 1.5 ml acetic acid and the resulting precipitate extracted with methylene chloride. The organic extract was evaporated and the residue which contained 4,5-methylenedioxy-7'-methyl-5',7',8',9'-tetrahydrospiro[phthalan-1,6'-1,3-dioxolo[4,5-h][3]benzazepine]-3-one was dissolved in 150 ml hot absolute alcohol and stored in an open flask for 3 days. The precipitated 4,5-methylenedioxy-7'-methyl-8',9'-dihydrospiro[phthalan-1,6'-1,3-dioxolo[4,5h][3]benzazepine]-3,5'[7'H]dion was isolated by filtration, 1.45 g, m.p. 195°–197° dec.

EXAMPLE 30

A solution of 1.1 g of 4,5-methylenedioxy-7'-methyl-8',9'-dihydrospiro[phthalan-1,6'-1,3-dioxolo[4,5-h][3]benzazepine]-3,5'[7'H]dion in 30 ml of tetrahydrofuran was treated at 0° with 0.2 g of lithium borohydride and then stored for 12 hours at room temperature. After evaporation of the solvent and addition of 20 ml water the solution which contained 5,6-cis-6[5-hydroxy-6,7,8,9-tetrahydro-7-methyl-5H-1,3-dioxolo-[4,5-h][3]benzazepin-6-yl]-2,3-methylenedioxy benzoic acid was heated for 5 min. on a steam bath. The cooled solution was treated with 2.5 ml of acetic acid and heated for 20 min. on the steam bath. After cooling and addition of conc. sodiumcarbonate solution, the precipitate was extracted with methylenechloride. The residue of the methylene chloride solution was recrystallized from methanol to yield rac. 4b,10b-cis-2,3,7,8-bismethylenedioxy-6-oxo-11-methylrheadan, m.p. 240–245° dec.

EXAMPLE 31

To a stirred solution of 0.367 g of 4b,10b-cis-2,3,7,8-bismethylenedioxy-6-oxo-11-methylrheadan in a mixture of 15 ml of absolute pyridine and 12 ml of absolute tetrahydrofuran at −70°was added dropwise 6.1 ml of a 3.5% tetrahydrofuran solution of sodium (bis-methoxyethyl)aluminum hydride. After 4 hr. at −70°, the reaction was stored at −18° overnight, decomposed by the addition of ice cold 1N-NaOH and extracted with methylene chloride. The organic extract was evaporated and the residue refluxed with a mixture of 2 ml of 5% NaOH and 20 ml of ethanol for 10 min. After evaporation of the alcohol, the residue was distributed between water and methylene chloride. The residue of the methylene chloride solution was chromatographed on silicagel (solvent CHCl₃) to yield 4b-S, 10b-S, 6-R and 4b-R, 10b-R, 6-S, 2,3-7,8 bismethylenedioxy-6-hydroxy-11-methylrheadan, m.p. 210° (from ether).

EXAMPLE 32

To 50 mg of 4b-S, 10b-S, 6-R and 4b-R, 10b-R, 6-S, 2,3-7,8 bismethylenedioxy-6-hydroxy-11-methylrheadan in 5 ml of abs. methanol, 1 ml of trimethylorthoformate and 1 drop of conc. sulfuric acid was added. After 5 min. at room temperature, 10 mls of saturated sodium carbonate solution was added and the precipitated extracted with methylene chloride. The methylene chloride residue was recrystallized from 30 ml of methanol to yield 4b-S, 10b-S, 6-R and 4b-R, 10b-R, 6-S, 2,3-7,8-bismethylenedioxy-6-methoxy-11methylrheadan, m.p. 222°–224°.

EXAMPLE 33

A solution of 4.27 g of 4,4',5'-trimethoxy-7'-methyl-8',9'-dihydrospiro[phthalan-1,6'-1,3-dioxolo-[4,5-h][3]benzazepine]-3,5'(7'H)-dione in 370 ml of glacial acetic acid was hydrogenated with 1 g of platinum oxide for 1 hour at room temperature and 2 atm. and then for 5 hours at 50° and 100 atm. After evaporation of the solvent under reduced pressure, the residue was dissolved in ice cold 2N-NaOH and extracted with methylenechloride. The aqueous alkaline solution was acidified with acetic acid and the 2.6 g that separated was recrystallized from 30 ml of ethanol to give 1.7 g of 5,6-trans-6(5-hydroxy-6,7,8,9-tetrahydro-4-methoxy-7-methyl-5H-1,3-dioxolo[4,5-h][3]benzazepin-6-yl)-2,3-dimethoxy benzoic acid, m.p. 225° dec.

EXAMPLE 34

A solution of 0.2 g of 6,7-trans-6(5-hydroxy-6,7,8,9-tetrahydro-4-methoxy-7-methyl-5H-1,3-dioxolo[4,5-h][3]benzazepin-6-yl)-2,3-dimethoxy benzoic acid in 5 ml of 1N-HCl was stored at room temperature for 24 hours. Addition of saturated sodium carbonate solution precipitated cis-4b,10b-2,3-methylenedioxy-4,7,8-trimethoxy-6-oxo-11-methylrheadan, m.p. 218°–200°.

What is claimed is:
1. A compound of the formula

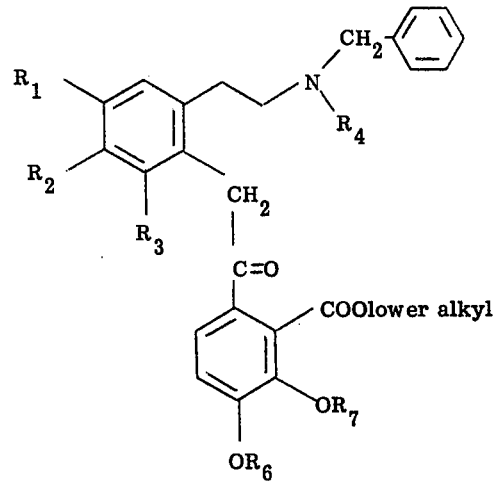

wherein $R_1$ and $R_2$ taken together are methylenedioxy; $R_3$ represents hydrogen or lower alkoxy; $R_4$ represents lower alkyl and $R_6$ and $R_7$ represent individually lower alkyl or when taken together are methylene.

2. A compound as in claim 1 of the formula 2,3-dimethoxy-6-(2-methoxy-3,4-methylenedioxy-6-benzylmethylaminoethylphenylacetyl)benzoic acid ethyl ester.

3. A compound as in claim 1 of the formula 2,3-dimethoxy-6-(3,4-methylenedioxy-6-benzylmethylaminoethylphenylacetyl) benzoic acid ethyl ester.

* * * * *